United States Patent
McLeod et al.

(10) Patent No.: US 6,686,144 B2
(45) Date of Patent: Feb. 3, 2004

(54) ADSORPTION OF POLYAMPHOLYTES TO CHARGED SURFACES AND ASSAYS INCORPORATING SAME

(75) Inventors: Kenneth J. McLeod, Stony Brook, NY (US); Nadine Pernodet, Stony Brook, NY (US); Miriam Rafailovich, Plainview, NY (US)

(73) Assignee: The Research Foundation of the State University of New York, Stony Brook, NY (US)

( * ) Notice: Subject to any disclaimer, the term of this patent is extended or adjusted under 35 U.S.C. 154(b) by 113 days.

(21) Appl. No.: 09/815,194

(22) Filed: Mar. 21, 2001

(65) Prior Publication Data

US 2002/0031758 A1 Mar. 14, 2002

Related U.S. Application Data

(60) Provisional application No. 60/190,806, filed on Mar. 21, 2000.

(51) Int. Cl.[7] .................................................. C12Q 1/00
(52) U.S. Cl. ............................ 435/4; 560/205; 562/598
(58) Field of Search ............................. 435/4; 560/205; 562/598

(56) References Cited

PUBLICATIONS

C.A. 109:146 231, Milich M.V et al, Vestnik Dermalologii i Venerologii 1988 (5) 25–32.*
Wong et al., "Electrically conducting polymers can noninvasively control the shape and growth of mammalian cells", *Proc. Natl. Acad. Sci. USA*, vol. 91, pp. 3201–3204 (1994).
Abstract: Denisova et al., "The influence of the chemistry of an organosilica surface on the adsorption of proteins from water–salt solutions", *Adsorpt. Sci. Technol.*, 17(3), 139–145 (1999).
Abstract: Vaynberg et al., "Structure and extent of adsorbed gelatin on acrylic latex and polystyrene colloidal particles", *J . Colloid Interface Sci.*, 205(1), 131–140 (1998).
Vaynberg et al., "Structure and Extent of Adsorbed Gelatin on Acrylic Latex and Polystyrene Colloidal Particles", *J. of Colloid and Interface Sci*, vol. 205, pp. 131–140 (1998).
Pankov et al., Integrin Dynamics and Matrix Assembly: Tensin–dependent Translocation of $\alpha_5 \beta_1$ Integrins Promotes Early Fibronectin Fibrillogenesis, *The Journal of Cell Biology*, vol. 148, No. 5, pp. 1075–1090 (2000).
Xu et al., "Long–Range Electrostatic Trapping of Single–Protein Molecules at a Liquid–Solid Interface", *Science*, vol. 281, pp. 1650–1653 (1998).
Lochhead et al., "Assessing the Role of Interfacial Electrostatics in Oriented Mineral Nucelation at Charged Organic Monolayers", *J. Phys. Chem. B*, 101(50), pp. 10821–10827 (1997).
Ohashi et al., "Dynamics and elasticity of the fibronectin matrix in living cell culture visualized by fibronectin–green fluorescent protein", *Proc. Natl. Acad. Sci.*, vol. 96, pp. 2153–2158 (1999).
Netz et al., "Complexation Behavior of Polyampholytes and Charged Objects", *Macromolecules*, 31, 5123–5141 (1998).
Dobrynin et al., "Adsorption of a Polyampholyte Chain on a Charged Surface", *Macromolecules*, 30, 4332–4341 (1997).
Kamiyama et al., "Effect of pH and Salt on the Adsoption and Interactions of an Amphoteric Polyelectrolyte", *Macromolecules*, 25, 5081–5088 (1992).
Sens et al., "Counterion Release and Electrostatic Adsorption", *Physical Review Letters*, vol. 84, No. 21, pp. 4862–4865 (2000).
Ellis et al., "Polyelectrolyte adsorption on heterogeneously charged surfaces", *J . of Chemical Physics*, vol. 112, No. 19, pp. 8723–8729 (2000).
Dobrynin et al., "Adsorption of Polyelectrolytes at an Oppositely Charged Surface", *Physical Review Letters*, vol. 84, No. 14, pp. 3101–3104 (2000).
Baneyx et al., "Self–assembly of fibronectin into fibrillar networks underneath dipalmitoyl phosphatidylcholine monolayers: Role of lipid matrix and tensile forces", *PNAS*, vol. 96, No. 22, pp. 12518–12523 (1999).
Ray et al., "Theory of Delocalized Ionic Binding to Polynucleotides: Structural and Excluded–Volume Effects", *Biopolymers*, vol. 32, pp. 541–549 (1992).
Dimilla et al., "Adsorption and Elution of Extracellular Matrix Proteins on Non–tissue Culture Polystyrene Petri Dishes", *J. of Colloid and Interface Sci.*, vol. 153, No. 1, pp. 212–225 (1992).
Neyret et al., "Adsorption of Polyampholytes on Polystyrene Latex: Effect on Colloid Stability", *J. Colloid and Interface Sci.*, vol. 176, pp. 86–94 (1995).
Alberts et al., "Multiple Forms of Fibronectin Are Produced by Alternative RNA Splicing", *Molecular Biology of The Cell*, Third Edition, p. 987 (1994).
Asthagiri et al., "Quantitative Relationship among Integrin–Ligand Binding, Adhesion, and Signaling via Focal Adhesion Kinase and Extracellular Signal–regulated Kinase 2", *J. of Biological Chemistry*, vol. 274, No. 38, pp. 27119–27127 (1999).

* cited by examiner

*Primary Examiner*—Paul J. Killos
(74) *Attorney, Agent, or Firm*—Dilworth & Barrese, LLP.

(57) ABSTRACT

Polyampholytes including fibronectin and aggrecan are made to aggregate and form fibrillar lattice networks environment free of cells, extraneous proteins and other materials which may be present in an extracellular matrix. A composition having sufficient charge density is utilized to cause aggregation and self-assembly of such polyampholytes and to provide an assay for determining the effects of environmental agents on such aggregation and self-assembly.

33 Claims, 12 Drawing Sheets

Fig. 2A     Fig. 2B
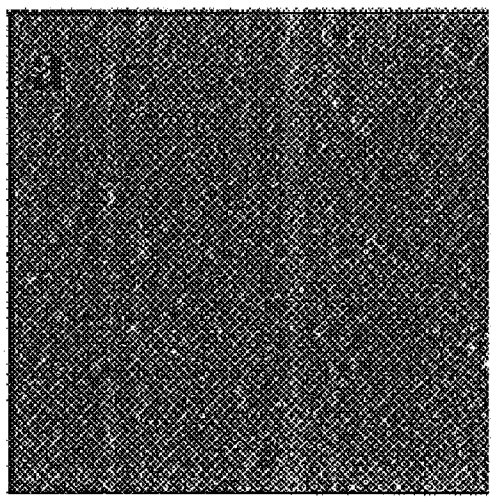 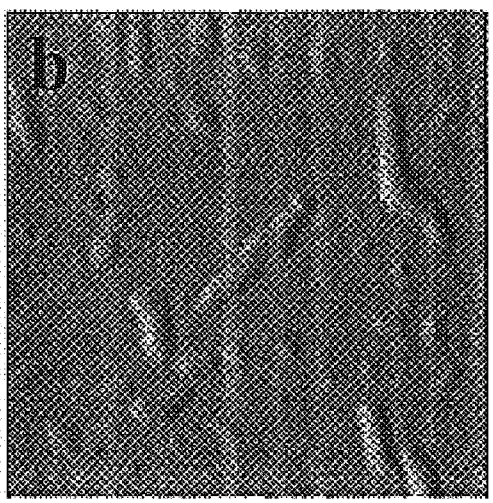
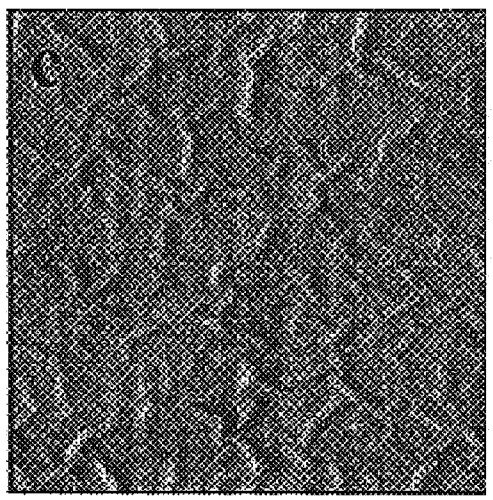 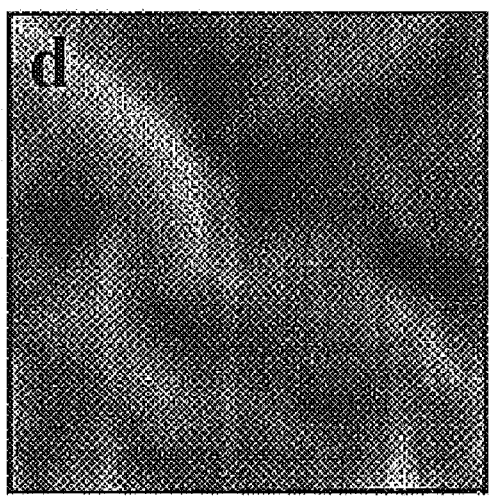
Fig. 2C     Fig. 2D

Albumin  FN  Aggrecan

Dimensions of the fibronectin network on PSS 23% after 41 hours and 72 hours with or without Electric Field.

ADSORPTION OF POLYAMPHOLYTES TO CHARGED SURFACES AND ASSAYS INCORPORATING SAME

CROSS REFERENCE TO RELATED APPLICATIONS

This application claims priority to U.S. Provisional application Serial No. 60/190,806 filed Mar. 21, 2000, the contents of which are hereby incorporated by reference.

GOVERNMENT INTERESTS

This invention was funded, at least in part, under grants from the National Institute of Environmental Health Grant No. RO1-ES07803 and the National Science Foundation MRSEC, Grant No. DMR-9632525. The Government may therefore have certain rights in the invention.

BACKGROUND

1. Technical Field

The present invention relates to the adsorption of polyampholytes to charged surfaces to form matrices. More particularly, surface charged density of a synthetic material is manipulated to effect assembly and matrix formation polyampholytic molecules.

2. Description of Related Art

During tissue development, repair and adaptation, the behavior of cells is largely controlled by interactions with their extracellular matrix (ECM). While the local cell population synthesizes the bulk of the extracellular matrix material, the ECM, correspondingly, influences cell phenotypic expression by providing attachment sites which modulate cell morphology and intracellular signal transduction events. The result of this pas-de-deux is a tissue with the requisite structural and functional capabilities. While the dramatic influences of subtle changes in matrix conformation are well demonstrated in Weaver, et al., *J. Cell Biol.* 137, 231–245 (1997), an understanding of the processes regulating the deposition and remodeling of the ECM forms the basis of much of the current research in developmental biology. Cells can play a critical role in the organization of the ECM, but physico-chemical dynamics carry the dominant responsibility for the nucleation, initiation and formation of the matrix.

The prototypical example of ECM organization remains that of collagen. The self-assembly of solubilized collagen to form gels was demonstrated close to 50 years ago Gross, et al., *Proc. Soc. Exp. Biol. Med.* 80, 462 (1952), Gross, et al., *J. Biol. Chem.* 233, 355–360 (1958). The triple helical collagen molecule spontaneously assembles under appropriate pH and ion conditions to form fibrils 20 nm to 100 nm or greater in diameter, and subsequently into fibril bundles as large as several hundred micrometers in diameter, Wood, et al., *Biochem. J.* 75, 588 (1960), Birk, et al., in *The Cell Biology of the Extracellular Matrix*, E. D. Hay, Ed. (Academic Press, New York, 1991) pp 221. The local cell population also plays an important role in this organizational process, both by secreting cross-linking enzymes, and by mechanically organizing the collagen fibers through attachment and contraction, Bell, et al., *Proc. Natl. Acad. Sci. USA* 76(3), 1274–1278 (1979), Kleinman, et al., *Analytical Biochemistry* 94, 308–312 (1979).

The organization of other major ECM molecules such as fibronectin, tenascin, and titin, remains far less well understood. Fibronectin, for example, is known to assemble into fibrils 100–1000 nm in diameter, but will not do so spontaneously in solution, generally requiring the presence of cells or cell-surface-like structures, Hynes, *Proc. Natl. Acad. Sci. USA* 96(6), 2588–2590, (1999). Fibronectin is an adhesive protein, acting as the primary intermediate between cells and the collagen matrix for many cell types. It is a large ($M_w$=450–500 kDa) glycoprotein, consisting of two nearly identical covalently linked subunits, each composed of three types of repeating modules. This complex forms a globular tertiary structure in solution, but an elastic, extended structure when formed into fibrils, Christopher, et al., *J. of Cell Science* 110, 569–581, (1997); Krammer, et al., *Proc. Natl. Acad. Sci. USA* 96(4), 1351–1356, (1999). However, the forces that provide the extension of the globular molecule into a fibrillar structure in the presence of cells remain undefined. Recent work suggests that plasma membrane lipid domain expansion could provide this necessary force for fibril assembly though the applicability of this proposed mechanism to the physiologic condition remains unclear, Pankov, et al., *Mol. Biol. Cell* 10, 4A–4A, (1999), Baneyx, et al., *Proc. Natl. Acad. Sci. USA* 96(22), 12518–12523, (1999).

Under in vivo conditions, fibronectin is a highly charged macromolecule with a net negative charge of approximately 47 (pI=5.6–6). While this molecule appears to have a cylindrical shape in solution, the contour of this molecule in the unfolded state has been visualized by electron microscopy, and these studies indicate a globular strand-like molecule approximately 2 nm in diameter and 140 nm in length, Petersen, et al., (1989) *Fibronectin*, Academic Press, NY. pp. 1–25. These dimensions would suggest that the molecule presents an average surface charge density of approximately 0.025 C/m$^2$. The inherent difficulty in understanding fibronectin adsorption and fibrillogenesis is the identification of the process by which these net negatively charged molecules not only adsorb onto negatively charged substrates with charge densities of 0.1 C/m$^2$ or more, but undergo multilayer adsorption. Moreover, given that the Debye screening length at physiologic salt concentrations is on the order of only 10 angstroms, it is important to address how substrate surface charge density can influence the formation of fibrillar structures as large as one micrometer in diameter.

The adsorption of charged polymers and polyelectrolytes onto both uniformly and non-uniformly charged surfaces, has been analyzed both experimentally and theoretically, Fleer, et al., (1993), *Polymers at Interfaces*; Chapman and Hall: London, Dobrynin, et al., (1999), Phys. Rev. Ltrs. 84, 3101–3104, Ellis, et al., (2000), *J. Chem. Phys.* 112:8723–8729, Sens, P. et al., (2000), Phys. Rev. Ltrs. 84, 4862–4865. However, while proteins commonly support a net charge (typically negative), they are polyampholytic in character, that is, after dissociation in a physiologic medium proteins support both positive and negative charge domains. Though the theory of polyampholyte adsorption remains relatively undeveloped, there have been substantial experimental efforts in this area due to the relevance of protein adsorption processes in technologies such as photography, Vaynberg, et al., (1998), *Colloid Interface Sci.* 205:131–140. These studies have shown that adsorption can occur even when both the protein and surface have the same net (negative) charge, Kamiyama, et al., (1992), *Macromolecules* 25:5081–5088, Neyret, et al., (1995), *J. Colloid Sci.* 176:86–94. Theoretical studies of single chain polyampholyte adsorption suggest that such adsorption can occur due to the polarization of the polymer chains in the electric field created by the charged surface, Dobrynin, et al., (1997), *Macromolecules* 30:4332–4341, Netz, et al., (1998), Macromolecules 31, 5123–5141. Recently, these theories have been extended to address multilayer adsorption of polyampholytes, Dobrynin, et al., (1999), *Macromolecules* 32:5689–5700.

Notwithstanding the above, it is widely believed that assembled forms of fibronectin, unlike fibrillar collagen molecules which can be made to assemble into fibrils in a test tube, will assemble into filaments only on the surface of certain cells, suggesting that additional proteins are needed for filament formation. See, e.g., Alberts et al., Molecular Biology of the Cell, 3$^{rd}$ Ed., Garland Publishing, (1994) pg. 987.

The ECM serves as an important influence in the normal processes of growth, repair, and adaptation as well as in the development of disease states and cell transformation. An understanding of how environmental agents can influence ECM formation would be extremely beneficial in the efforts to identify harmful or beneficial environmental agents. The ability to create ECM-like structures in environments free from cells and undesirable proteins and/or peptides would provide a tremendous tool in the study of ECMs and the interactions of various substances and stimuli with ECMs.

SUMMARY

A method for causing aggregation of a polyampholyte selected from the group consisting of fibronectin molecules and aggrecan molecules is provided which includes subjecting the polyampholyte molecules to a charge density of greater than about 0.01 $C/m^2$ generated by a non-living system to cause aggregation of the polyampholyte molecules.

Also provided is a composition including a synthetic surface having a charge density greater than about 0.01 $C/m^2$ in contact with a polyampholyte selected from the group consisting of fibronectin and aggrecan.

A method for assaying the effect of an agent on adsorption of a polyampholyte selected from the group consisting of fibronectin and aggrecan on a charged surface is also provided which includes providing a surface having a charge density greater than about 0.01 $C/m^2$; providing the polyampholyte; allowing the polyampholyte to contact the surface in the presence of the agent; and comparing a characteristic selected from the group consisting of rate of adsorption of the polyampholyte, morphology of the polyampholyte and combinations thereof, to a control sample which includes a surface having a charge density greater than about 0.01 $C/m^2$ and the polyampholyte. The agent may be chemical or physical.

A method for evaluating the potential of a polyampholyte to form a network is also provided which includes the steps of providing a surface having a charge density greater than about 0.01 $C/m^2$; providing an ampholyte; allowing the ampholyte to contact the surface; and examining the surface to determine whether the polyampholyte forms a network.

BRIEF DESCRIPTION OF THE FIGURES

FIG. 2a depicts Atomic Force Microscopy (AFM) imaged morphology of adsorbed fibronectin at 0.03 $C/m^2$ on a sulfonated polystyrene surface. The surfaces indicate a thin globular layer of fibronectin with peak heights of about 80 nm.

FIG. 2b depicts AFM imaged morphology of adsorbed fibronectin at 0.08 $C/m^2$ on a sulfonated polystyrene surface. The surfaces indicate a fusion of adsorbed protein globules with peak heights of about 150 nm.

FIG. 2c depicts AFM imaged morphology of adsorbed fibronectin at 0.12 $C/m^2$ on a sulfonated polystyrene surface. The surfaces indicate the initiation of fibril formation with peak heights of about 280 nm.

FIG. 2d depicts AFM imaged morphology of adsorbed fibronectin at 0.15 $C/m^2$ on a sulfonated polystyrene surface. The surfaces indicate an extensive fibronectin network with peak heights reaching about 1400 nm.

DETAILED DESCRIPTION

Figure 1:
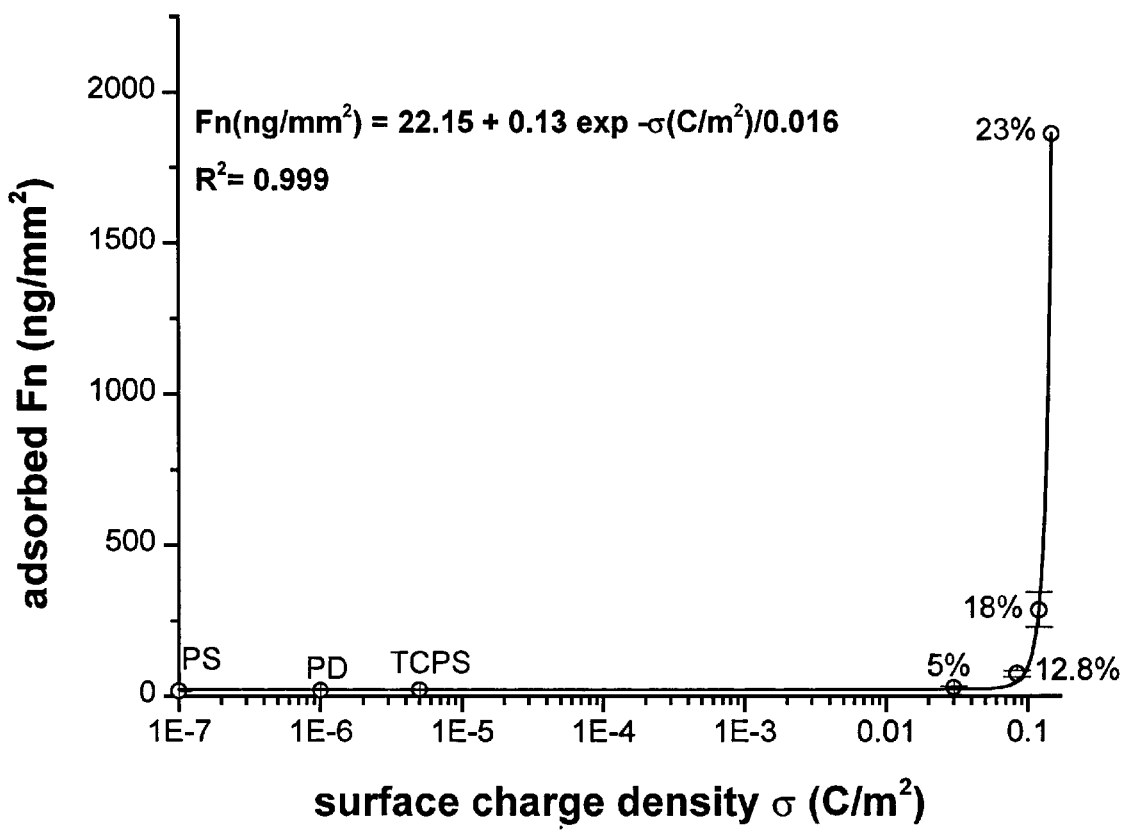
FIG. 1 is a graphic depiction of fibronectin adsorption as a function of surface charge density. $R^2$ is the correlation coefficient.

Formation of polyampholyte fibrillar networks independent of living cells, proteins and other ECM associated molecules is provided in accordance with the present invention. The characteristics of such polyampholyte fibrillar lattice networks can mimic naturally occurring ECMs. Accordingly, the present invention provides, for the first time, a modality with which to examine the behavior of specific polyampholyte ECM molecules per se and, further, the effects of various environmental agents on such molecules which allows extrapolation to the ECM as a whole. As used herein, the terms "lattice", "matrix" and "network" are interchangeable.

In accordance with the present invention, exposure of naturally occurring polyampholytes in solution to a charge density of greater than about 0.01 $C/m^2$ in connection with an adsorption surface causes adsorption of such polyampholytes on the surface. Adsorbed protein mass increases exponentially with increasing charge density. At charge densities over about 0.08 $C/m^2$, distinct fibrillar networks spontaneously form with a morphology similar to those observed to form in situ on cell surfaces. The self-organization process is time dependent.

As those with skill in the art will appreciate, the amount of charge density necessary to cause adsorption, assembly and fibrillogenesis of polyampholytes is variable and can be adjusted based on and is a function of salt concentration in a solution containing the polyampholyte. Specifically, in the case of monovalent salts, the critical charge density will decrease as the square root of the salt concentration. Thus, at monovalent salt, e.g., NaCl, concentrations of about 150 millimolar, the critical charge density ranges from about 0.08–0.1 $C/m^2$ to stimulate the outset of fibrillogenesis. Correspondingly, a similar result is obtained at a surface charge density of about 0.008–0.01 $C/m^2$ when the monovalent salt concentration is 1.5 millimolar. As those with skill in the art will also appreciate, various concentrations of di- and trivalent salts may be utilized to effect the degree of charge density necessary to cause adsorption, assembly and fibrillogenesis. It should be noted that, unless otherwise stated, for purposes of convenience, the salt concentration of fibronectin solutions used to deposit fibronectin onto charged surfaces is about 150 millimolar. While this is a preferred salt concentration, it should be considered as exemplary and not a limitation herein.

Preferred polyampholytes are fibronectin and aggrecan. Examples of other suitable fibril forming polyampholytes include vitronectin, tenascin, elastin and laminin.

The appropriate charge density is obtained by using charged materials such as polymers capable of generating and/or maintaining a charge density of about 0.01 $C/m^2$ or greater. In a preferred embodiment, the charge density is greater than about 0.1 $C/m^2$ and even more preferably greater than about 0.15 $C/m^2$ when the salt content of the fibronectin solution is about 150 millimolar. Sulfonated polystyrene is especially well-suited as a charge density source. Sulfonation levels of the sulfonated polystyrene can range from over 0% to about 30% or greater. A sulfonation level of about 23% provides a surface charge density of about 0. 15 $C/m^2$. It is contemplated that any material capable of supporting and/or generating a charge density range as described above may be used in accordance with the present invention. Examples of such materials are those containing functional charge groups. For example, negative charges may be imparted by sulfate groups, hydroxy groups, brominated groups, moieties, carboxyl groups and iodinated groups. Amide groups can be used to produce positively charged surfaces. Such functional charge groups can be placed on various known polymeric species by conventional methods known to those skilled in the art. Homopolymers of amino acids are also suitable, e.g., polylysine, which is negatively charged.

The charged material may be applied to a substratum or support layer to provide rigidity to the overall structure. Although the material used as the substratum should be inert to avoid unintended effects on the system which includes the charged material and polyampholyte, it is contemplated that the substratum may provide its own predetermined activity to affect the environment of the system with respect to various parameters such as charge density, humidity, temperature, pH and other variables. A preferred inert material is silicon. The substratum may be also flexible. The substratum may be of any suitable shape or thickness including flat, irregular, curved, round, square, etc. It is contemplated that various 3-dimensional structures are suitable such as sponge shapes, mesh, porous fabric, pegboard and the like. Examples of other materials which can be utilized to provide the substratum include mineral based substrates such as glass or quartz, metals such as gold, stainless steel and titanium, and polymers such as polyamides, polyurethanes, polysulfones, polycarbonates, acrylates and terephthalates.

It is contemplated that any method for depositing a suitably charged material onto the substratum known to those skilled in the art is appropriate for use herein. For example, charged polymers may be dissolved in a suitable solvent and applied by spin coating, dipping, spraying, vapor deposition and the like. For example, sulfonated polystyrene can be dissolved in dimethyl formamide and spin coated onto the surface of a silicon wafer.

In a preferred embodiment, flat, rigid, silicon wafers were coated with monodisperse sulfonated polystyrene (MW=282 kDa prior to sulfonation) films. The surface charge density in aqueous media was controlled by varying the degree of sulfonation, providing charge densities from 0 to about 0.15 $C/m^2$. In addition, adsorption onto two commonly utilized culture substrates, bacteriologic grade polystyrene petri dishes (PD), and tissue culture grade polystyrene dishes (TCPS), which support net surface charge densities in the range of $10^{-6}$–$10^{-5}$ $C/m^2$ was evaluated.

Fibronectin adsorption onto the various surface coated substrates was characterized both biochemically and using atomic force microscopy. In initial experiments, fibronectin was allowed to adsorb for two days onto the surfaces. At monovalent salt concentrations of about 150 millimolar, the mass of fibronectin adsorbed was observed to be essentially independent of surface charge density for densities up to 0.03 $C/m^2$, as no significant differences in total fibronectin adsorption were found between pure PS surfaces (i.e. essentially zero charge density surfaces), PD, TCPS, or 5% polysulfonated coatings (0.03 $C/m^2$) (FIG. 1). A total protein adsorption of approximately 22 ng/$mm^2$ was observed in this range, in good agreement with previous results suggesting monolayer adsorption of fibronectin, Asthagiri, et al., *J. Bio. Chem.* 274(38), 27119–27127 (1999).

At higher surface charge densities, fibronectin adsorption enters a transition region where the total adsorbed fibronectin increases significantly with small increases in surface charge density. At a charge density of 0.15 $C/m^2$ total protein adsorption approaches 150 ng/mm$^2$. The adsorption over the full experimental charge density range ($10^{-7-0.15}$ C/m$^2$) closely follows an exponential dependence on charge density.

Increased surface charge density induced not only a rapid increase in the mass of fibronectin adsorption, but also a dramatic change in adsorbed protein morphology. Atomic force microscopy (AFM) images of the surfaces show that, on a pure polystyrene surface (charge density ~0 C/m$^2$), only a uniform adsorption layer of fibronectin is evident after three days of incubation. Fibronectin appears in a globular form on 0.03 C/m$^2$ as well as on 0.08 C/m$^2$ surfaces, though on the latter, globules are increased in size and small fibril-like structures are observed (See FIGS. 2a–2d). With increasing surface charge density a progressively more extensive fibrillar matrix of fibronectin evolves. On 0.12 C/m$^2$ and 0.15 C/m$^2$ surfaces, adsorbed fibronectin forms a distinct network. On the 0.15 C/m$^2$ polysulfonated surface, fibrils up to 10 $\mu$m wide, 40 $\mu$m long, and close to 1 $\mu$m high can be imaged by AFM. The morphologic characteristics of these fibrillar networks are remarkably similar both to those assembled on cell surfaces in vitro, Ohashi, et al., *Proc. Natl. Acad. Sci. USA* 96, 2153–2158, (1999) and those found to assemble on deformable biomimetic surfaces, Pankov, et al., *Mol Biol. Cell* 10, 4A—4A, (1999), Baneyx, et al., *Proc. Natl. Acad. Sci. USA* 96(22), 12518–12523, (1999).

Figure 3:
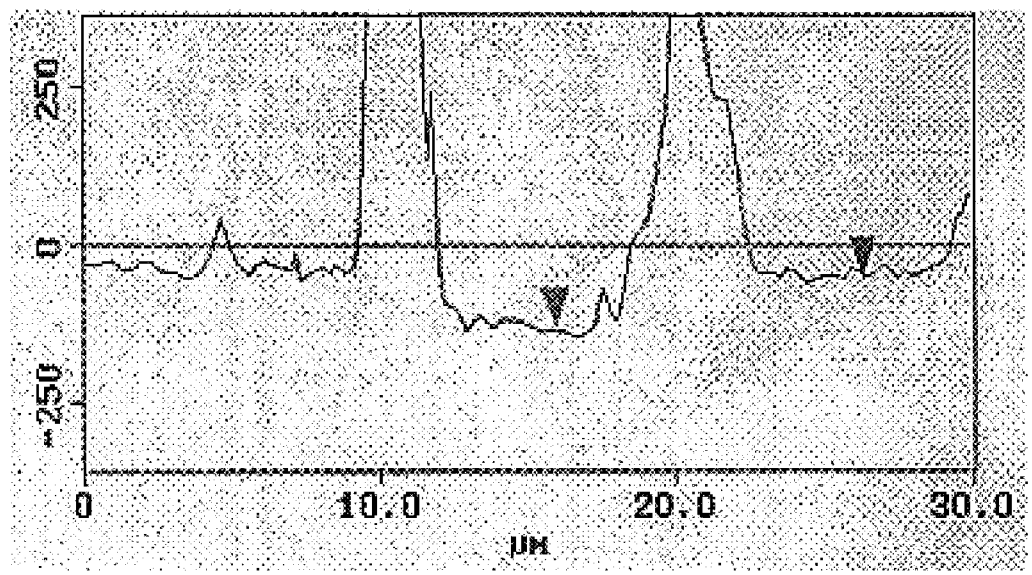
FIG. 3 depicts measurement of fibronectin base layer thickness.
Figure 4:
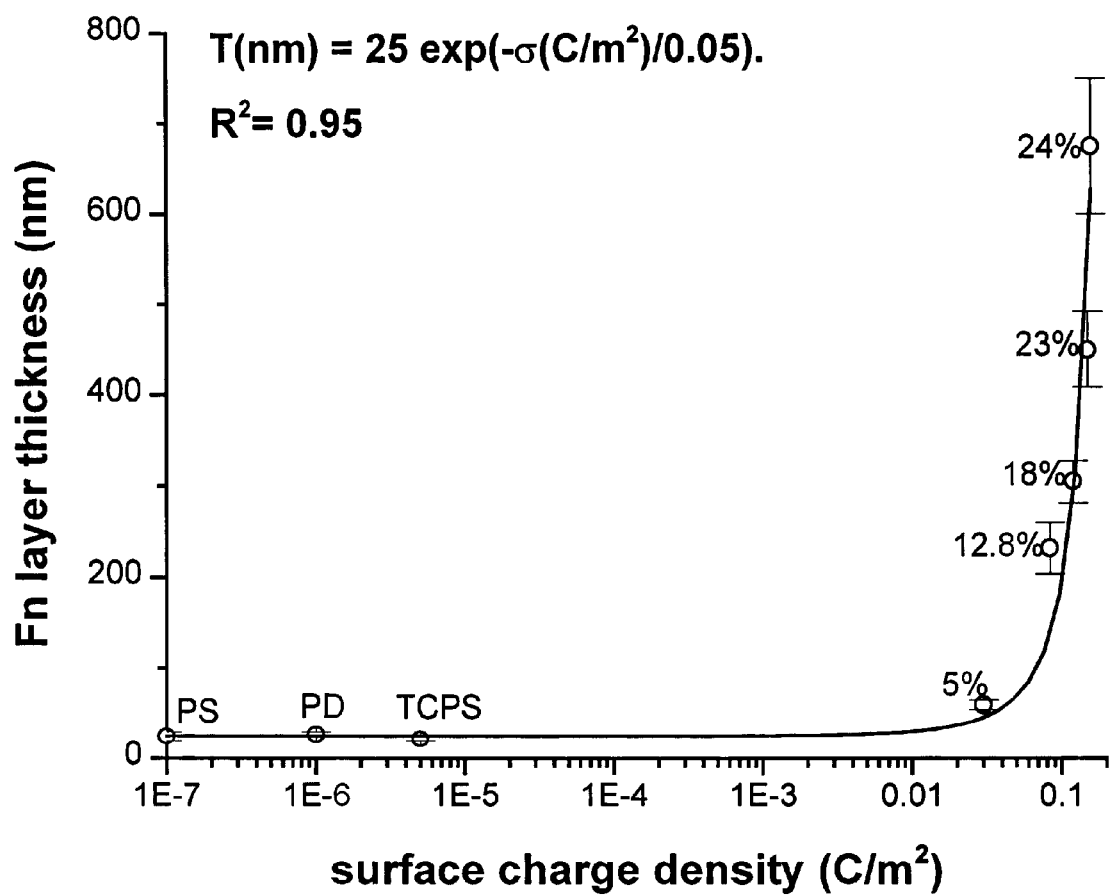
FIG. 4 is a graphic depiction of the thickness of adsorbed fibronectin as a function of surface charge density.
Figure 5:
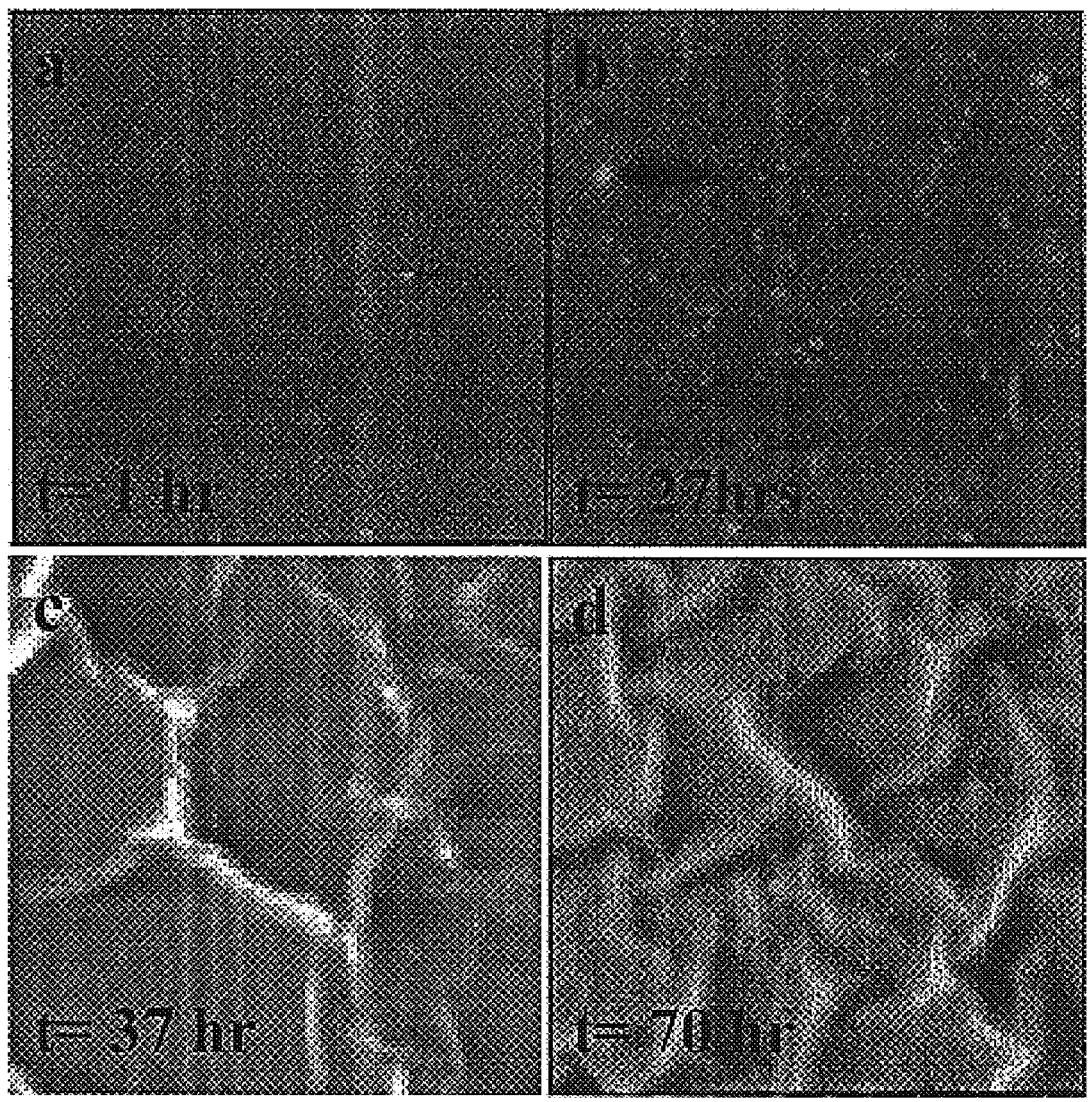
FIG. 5a depicts AFM imaged morphology of adsorbed fibronectin at 0.15 $C/m^2$ on a sulfonated polystyrene surface after one hour. Height of the fibronectin is about 50 nm.
FIG. 5b depicts AFM imaged morphology of adsorbed fibronectin at 0.15 $C/m^2$ on a sulfonated polystyrene surface after 27 hours. Peak height is about 100 nm.
FIG. 5c depicts AFM imaged morphology of adsorbed fibronectin at 0.15 $C/m^2$ on a sulfonated polystyrene surface after 37 hours. Peak height is about 150 nm.
FIG. 5d depicts AFM imaged morphology of adsorbed fibronectin at 0.15 $C/m^2$ on a sulfonated polystyrene surface after 70 hours. Peak height is about 1400 nm.

AFM imaging also permitted a measurement of the adsorbed protein layer thickness in regions between the fibrillar structure (FIG. 3). For surfaces with charge densities up to 0.03 C/m$^2$, a uniform adsorbed layer thickness of approximately 25 nm was measured (FIG. 4). The thickness of this monolayer is intermediate in terms of the cited cylindrical dimensions for fibronectin (i.e. height of 60 nm and base dimension of 6 nm). DiMilla, et al., *J. of Colloid and Interface Science* 153(1), 212–225, (1992). This suggests that a mixed orientation of molecules are adsorbing onto the surface, or that a strong surface interaction is forcing the molecules to partially unfold.

With increasing surface charge density, fibronectin layer thickness is also seen to increase abruptly, from 60 nm for 0.03 C/m$^2$ surfaces to 675 nm for 0.158 C/m$^2$ surfaces, at an incubation time of 47 hours. Thickness measurements of the adsorbed multilayer also approach exponential behavior (FIG. 4), but with a denominator in the exponential growth term (0.05 C/m$^2$) substantially different from that observed in the protein adsorption fit (0.016 C/m$^2$). This may be an indication that molecular conformation of the fibronectin changes with increasing adsorption layer thickness.

Figure 6:
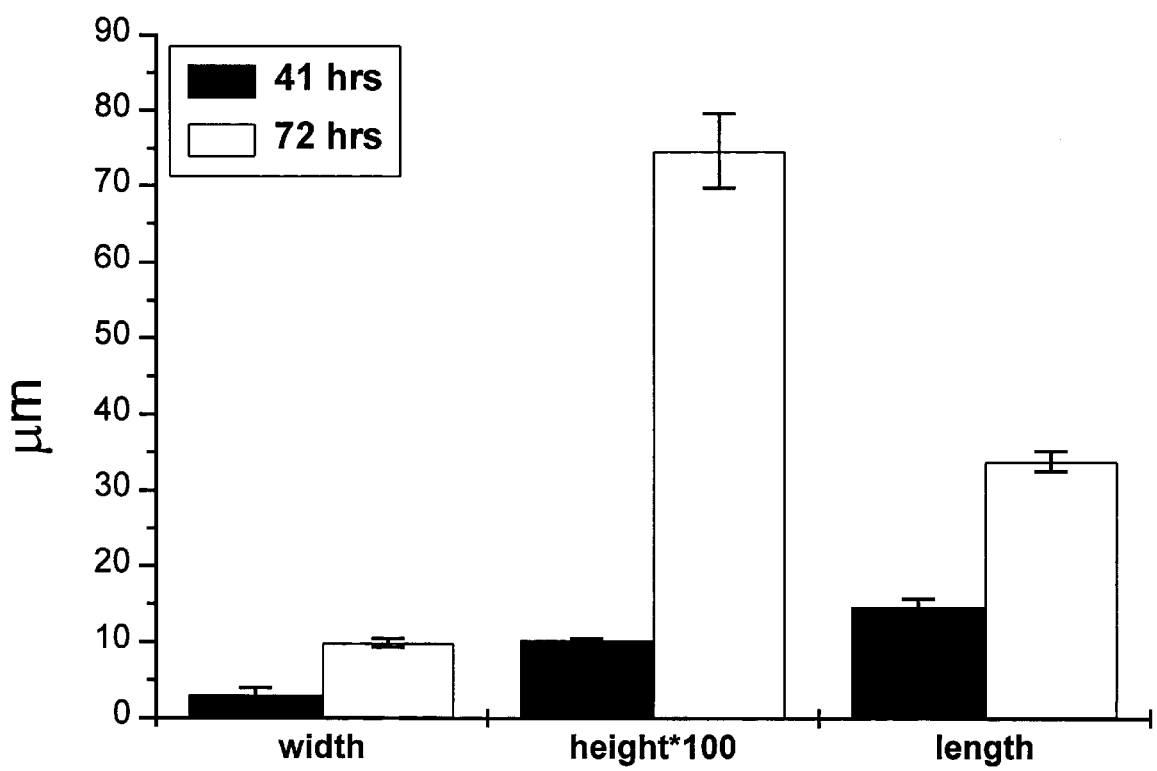
FIG. 6 is a graphic depiction of the evolution of fibronectin fibril structure between 41 hours and 72 hours incubation on $-0.15$ $C/m^2$ surfaces. Width, height and length measures were obtained from digitalized AFM images (N=80 fibrils). Height reflects distance above the adsorbed base layer of fibronectin.

The fibronectin network formation on a 0.15 C/m$^2$ surface was followed as a function of time to observe the progression in network formation (FIGS. 5a–5d). At the earliest time point measured, (1 hour) adsorbed protein levels were at 50–60 ng/mm$^2$, a level that did not significantly increase for the next 3 hours. However, over the subsequent 5 days adsorbed protein levels continued to increase monotomically, exceeding 200 ng/mm$^2$ by day 5. Correspondingly, the formation of the fibrillar network progressed slowly for at least the first 24 hours, at which point the initial strands of fibrils were just becoming evident as protein globules. At 27 hours the peak height was about 100 $\mu$m. By 36 hours, few globules remain, and fibril interconnections have increased. Large area scans show that these fibrils have begun to self-organize into a lattice. This time is comparable with that reported by Ohashi et al., supra, who observed a 36 hour time was required for the formation of a fibronectin matrix in presence of cells. At 37 hours peak height was about 150 $\mu$m. After 70 hours, the fibronectin lattice is seen to cover the entire surface of the sample. Comparison of the average morphologic characteristics of fibrils between 41 and 72 hours demonstrates significant increases in length, width and height (FIG. 6). Following 72 hours of adsorption typical fibrils have achieved dimensions of about 30–50 $\mu$m in length, 10 $\mu$m wide and 1.5 $\mu$m in height. In FIGS. 5a–5d the scanned image area was 50×50 $\mu$m. The fibronectin networks formed on the sulfonated polystyrene substrates were found to be stable for up to 5 days and remained irreversibly adsorbed on the surface as evidenced by the fact that when surfaces with fibronectin networks were placed in a PBS solution lacking fibronectin, network morphology was stable. Measurements of the baselayer thickness on 0.15 C/m$^2$ surfaces after 100 hours yielded similar values to those found at 48 hours.

Figure 7A:
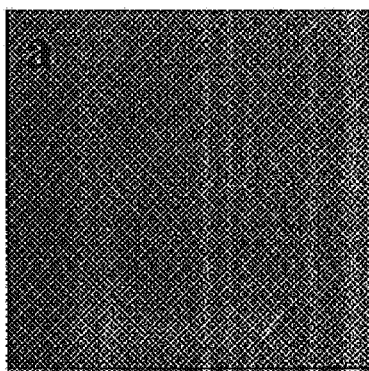
FIG. 7a depicts AFM imaged morphology of albumen at $-0.15$ $C/m^2$ on a sulfonated polystyrene surface at 70 hours. Peak heights are about 20 nm.
Figure 7B:
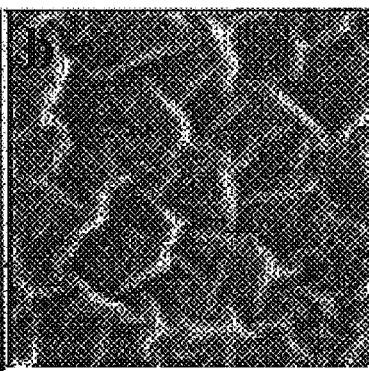
FIG. 7b depicts AFM imaged morphology of fibronectin at $-0.15$ $C/m^2$ on a sulfonated polystyrene surface at 70 hours.
Figure 7C:
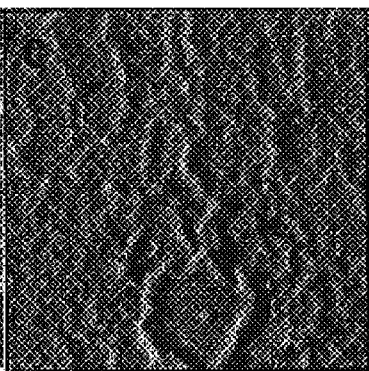
FIG. 7c depicts AFM imaged morphology of aggrecan at $-0.15$ $C/m^2$ on a sulfonated polystyrene surface at 70 hours. Peak heights are about 950 nm.

To determine whether the influence of the high surface charge on matrix formation generally applicable to the organization of other ECM molecules similar adsorption experiments were repeated with albumin ($M_w$=6.6.10$^3$), a globular and low charge density protein, and aggrecan ($M_w$>2.5.10$^6$), a large and high charge density protein. Following 70 hours of incubation, adsorbed proteins were imaged on 0.15 C/m$^2$ surfaces (FIGS. 7a–7c). While total adsorbed albumen increased with increasing surface charge density, the adsorbed layers were consistently observed to form a uniform layer on this surface, with no evidence of formation of a network. Conversely, aggrecan did form a network with dimensions and an organization very different to that of the fibronectin network formed on similar high charge density surfaces. With respect to FIGS. 7a–7c, protein/PBS solutions were incubated for 70 hours at 37° C. and 100% humidity. The scanned area was 100×100 $\mu$m.

The mechanism by which charge density triggers the abrupt transition to multilayer protein adsorption, and as importantly, fibril formation of these large ECM proteins remains unclear. Without wishing to be bound by any theory, it may be that several phenomena associated with colloidal interactions and/or polyelectrolyte effects are playing a critical role in this process. The high charge density at which multilayer adsorption and network formation were observed would be associated with a concentrated cation double layer extending several tens of nanometers above the surface, and so in this region H$^+$ and Na$^+$ ion concentration would be significantly enhanced. Both the drop in pH, or the high local Na$^+$ concentration could result in sufficient morphologic changes in the protein molecules to alter adsorption kinetics and equilibria. Such pH effects, for example, have been implicated in the acceleration of mineralization at highly charged interfaces, Lochhead, et al., *J. Phys. Chem.* B 101(50), 10821–10827, (1997). Closely related to these electrical double layer phenomena are excluded volume effects. At high charge densities counter-ions may be excluded from, or demonstrate a reduced diffusivity near the surface region resulting in the double layer extending to greater distance into the media, with corresponding effects also extending away from the surface and further into the solution, Xu et al., *Science* 281, 1650–1653, (1998). Indeed, if the adsorbed species supports a net charge similar to that of the surface, double layer growth would be exacerbated with each additional monolayer of adsorbed protein, Ray, et al., *Biopolymers* 32, 541–549 (1992). Alternatively, the abrupt onset of multilayer adsorption and network formation at high charge density may reflect the increasing influence of correlative attractive forces, Grieldbrand, et al., *J. Chem. Phys.* 80(5), 2221–2228 (1984). At high charge densities, uniformity of the charge layer is unlikely, and inhomogeneities can give rise to attractive double layer interactions, interactions between surface layers, and domain correlations.

Extending these theories to the case of fibronectin suggests that the cylindrical shape of the folded fibronectin molecule in solution is consistent with the shape being a function of chain entropy, fluctuation induced attractive forces between positive and negative charge domains, and, the overall Coulomb repulsion between the excess negative charges, Dobrynin, et al., (1997) Macromolecules 30:4332–4341. In the presence of the sulfonated polystyrene surface, the electric field created by the negative surface charge will serve to change the protein conformation into a more elongated structure, polarize the molecules, and expose positive domains for adsorption. Despite the net negative charge of the molecules, the adsorption of fibronectin to the negatively charged substrate is, therefore, largely electrostatic, the positive charge domains on the fibronectin molecule serving as the counterions to the substrate charge. The shape of the molecule adsorbed onto the surface will be dependent on the substrate charge density, with molecules weakly adsorbing onto low charge density surfaces through a few positive domains, with the remainder of the molecule taking on a loose or unstructured conformation. However, at increasing charge densities, most of the positive charge domains will be adsorbed onto the substrate and negative charge domains will be driven away from the surface, creating a highly structured sandwich-like conformation. This conformation serves to concentrate the negative charge domains at a plane above the substrate. Given that fibronectin supports an average net negative charge density close to 0.025 $C/m^2$, a four to five fold concentration of the negative domains above the surface would result in the creation of a new adsorption "surface" with a charge density exceeding 0.1 $C/m^2$. It is evident how increasing surface charge density can lead to the abrupt transition to multilayer adsorption.

In summary, the observation of an abrupt transition to multilayer fibronectin adsorption and spontaneously formed fibronectin networks on a charged surface, in the absence of cells, membrane receptors or deformable lipid layers, indicates that high charge density, per se, is sufficient to initiate the nucleation and growth of fibronectin fibrils. The networks observed are similar to the networks induced by the presence of cells, and most importantly, the surface charge densities required to initiate network formation are comparable to the surface charge density of cells. Moreover, like fibronectin, most major ECM proteins are polyampholytic (polyelectrolytes containing both positive and negative charges) colloids.

Any organic polyampholyte (i.e., those which support both positive and negative charges) can be utilized to interact with the requisite charge density according to the present invention to determine whether adsorption occurs, the rate of adsorption, the degree of adsorption, and the morphology of polyampholyte in the adsorbed state. Such morphology includes topography, thickness of the base layer, and characteristics of fibril structure including periodicity. Moreover, the effect of various agents can be determined by including such an agent(s) in the mixture which includes a polyampholyte and the surface having a charge density greater than about 0.03 $C/m^2$. Such agents may be chemical or physical and include, carcinogens, therapeutic agents, mutagens, toxins, living organisms, dead organisms, electromagnetism, and the like. For example, the effects of pH, temperature, bacteria, viruses, heavy metals and/or electromagnetic fields on extracellular matrix formation can be assayed in accordance with the present invention. As used herein, the term therapeutic agent is used in its broadest sense and includes any substance or mixture of substances which may have any clinical use such as a drug or diagnostic agent. For example, growth factors, enzymes, hormones, releasable dyes, can be assayed in accordance with the present disclosure.

In addition to scanning probe/atomic force microscopy (AFM), those skilled in the art will recognize that other visualization or scanning methods may be utilized in accordance with the present invention. For example, electron microscopy, infrared spectroscopy, UV raman scattering, and other modalities which may for example measure electrochemical, optical, mass and thermal changes may all be appropriate. AFM typically requires a substantially atomically smooth surface for which the spin-coated silicon wafers are particularly suitable.

Figure 8:
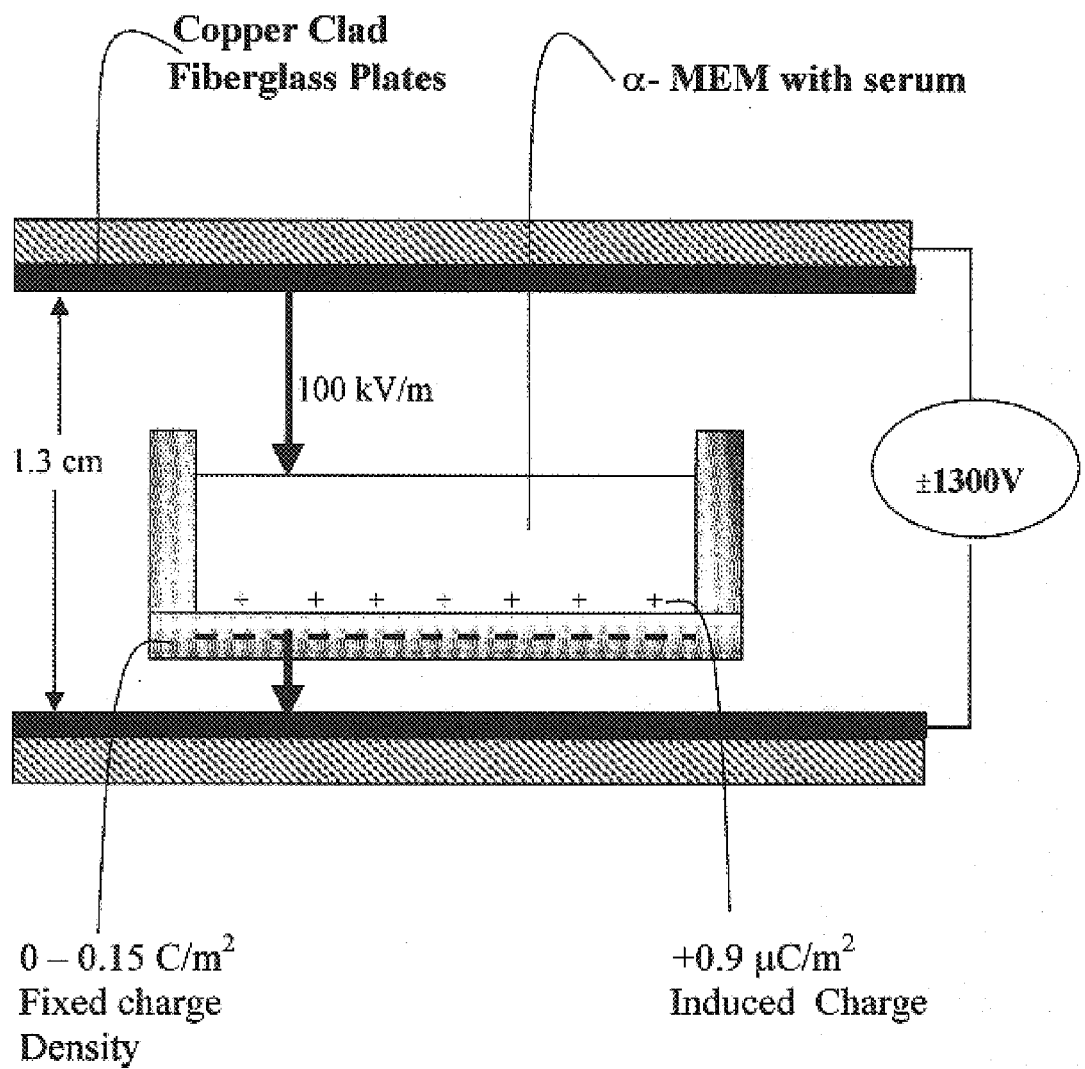
FIG. 8 illustrates placement of a sulfonated polystyrene surface into a parallel plate capacitor.

In one embodiment, the effects of an induced electric field on fibronectin adsorption was determined. FIG. 8 illustrates placement of sulfonated polystyrene surfaces into what is essentially a parallel plate capacitor between which an electric field of 0–100,000 V/m can be imposed. The samples have a small rubber ring placed on them which is used to confine a salt solution (phosphate buffered saline) which contains the protein (fibronectin) at a concentration of 10–100 micrograms per millilitre. The fixed charge density on the substrate can be controlled to be from 0–0.15 Coulombs per meter square, though in the data reported here all studies were done at 0.15 $C/m^2$. The applied field imposes an addition surface charge onto the substrate which is proportional to the dielectric permittivity of air and the applied electric field (i.e. $8.8 \times 10^{12}$ f/m×100,000 KV/m) or about 0.9 microCoulomb per square meter. This perturbation, therefore, is about 1 part in 10 million, with respect to the fixed charge density of the sulfonated polystyrene surface. The sign of this perturbation can be varied to be either positive or negative so as to test whether the adsoption demonstrates intrinsic non-linearity. It is preferred that incubations are at 37° C. in a 100% humidity environment.

Figure 9A:
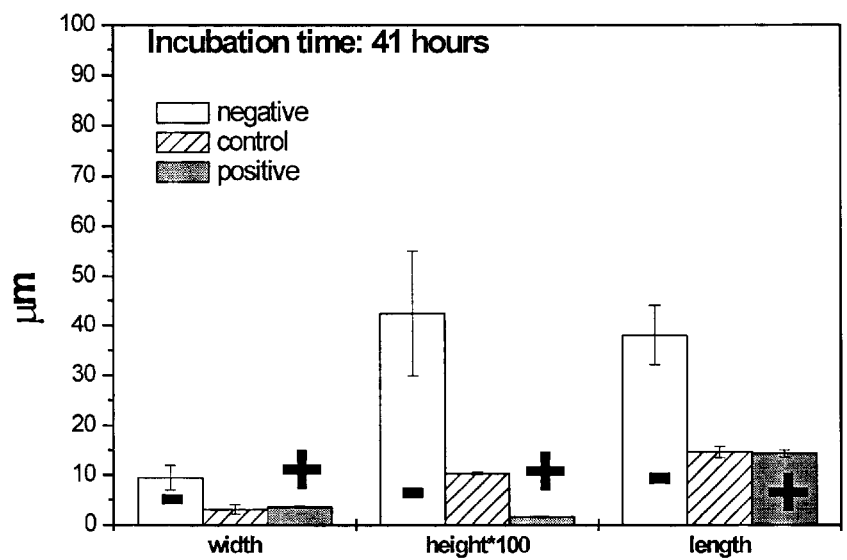
FIG. 9a is a graphic depiction of the effect of induced negative and positive charge on fibronectin matrix formation at 41 hours incubation on a $-0.15$ $C/m^2$ sulfonated polystyrene surface.
Figure 9B:
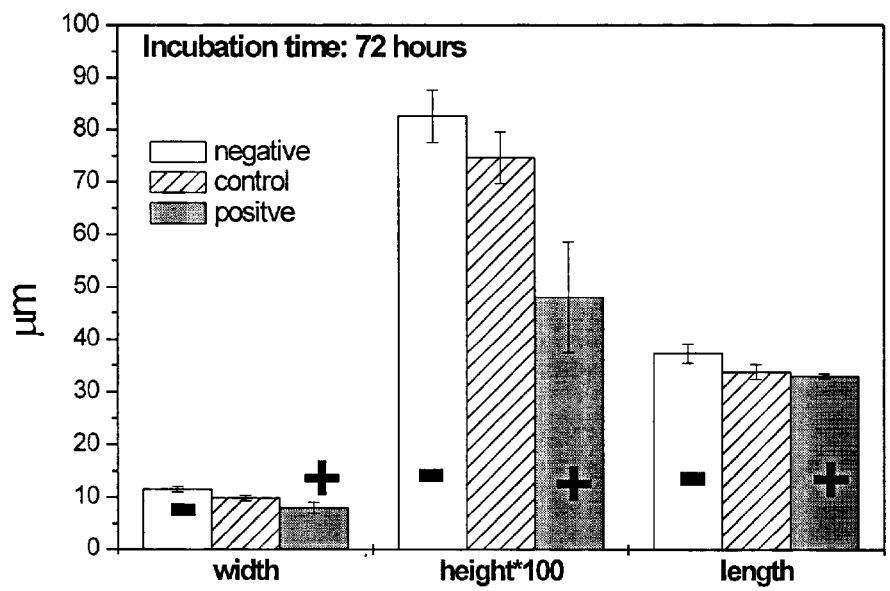
FIG. 9b is a graphic depiction of the effect of induced negative and positive charge on fibronectin matrix formation at 72 hours incubation on a $-0.15$ $C/m^2$ sulfonated polystyrene surface.

FIGS. 9*a* and 9*b* show that this small induced charge significantly altered the morphology of fibronectin matrix which forms on a 23% sulfonated surface (0.15 $C/m^2$ surface). Enhanced negative surface charge results in longer, taller and wider fibers, while a decreased negative charge (i.e. induced positive charge) results in only small changes at 41 hours of matrix growth, but significantly small fibers by 72 hours.

Figure 10A:
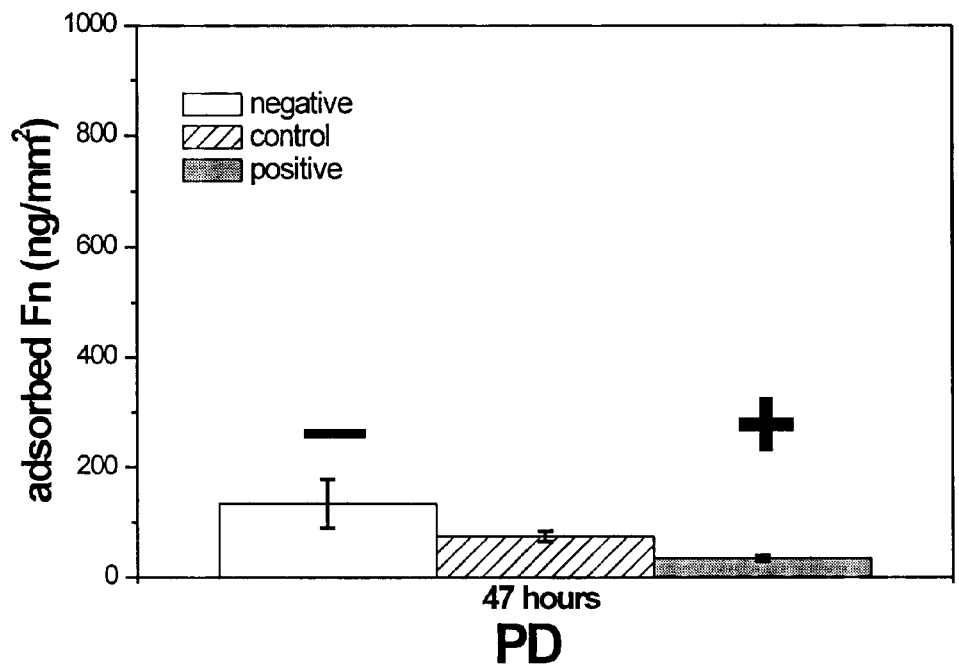
FIG. 10a is a graphic depiction of the effect of induced positive and negative charge on fibronectin adsorption at 47 hours on a polystyrene surface (bacteriologic grade).
Figure 10B:
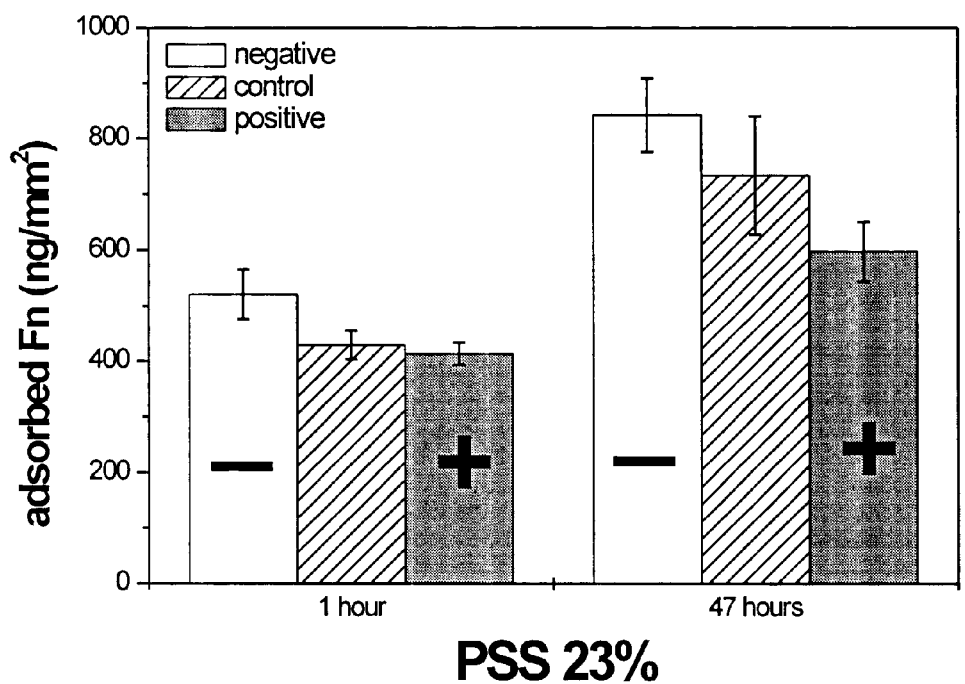
FIG. 10b is a graphic depiction of the effect of induced positive and negative charge on fibronectin adsorption at 1 hour and 47 hours on a 23% sulfonated surface (0.15 $C/m^2$).

FIGS. 10*a* and 10*b* show the results of biochemical assays of total adsorbed fibronectin, again demonstrating the same basic pattern, though this bioassay indicates a significant response of the system within 1 hour of the start of incubation.

The sensitivity of this system to small perturbations makes it ideal as the basis for numerous biosensors. Not only do small environmental perturbations cause dramatic changes in the matrix formation, but these changes are easily "read out", either in real time using optical methods or electrical methods, or after an acute exposure in which case a simple biochemical assay is utilized.

Figure 11A:
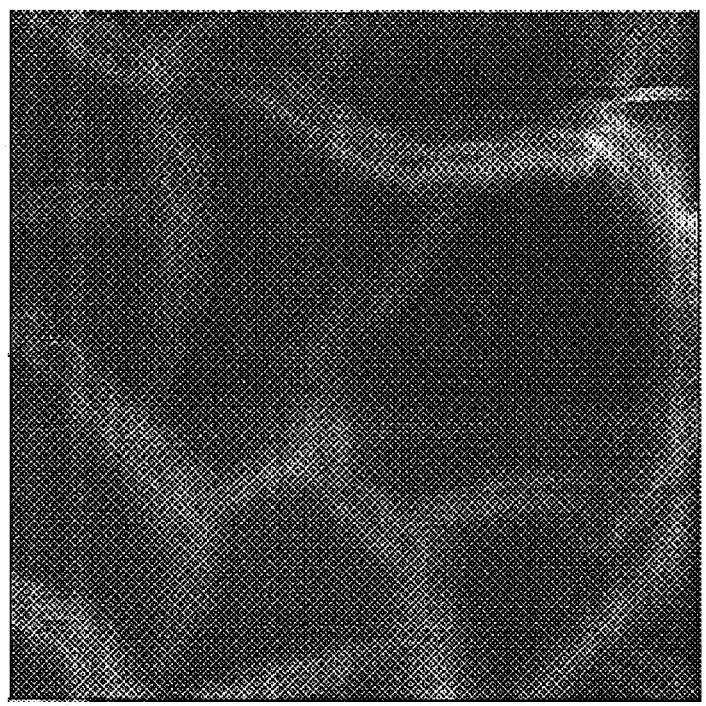
FIG. 11a depicts AFM imaged morphology of adsorbed fibronectin at 0.3 $C/m^2$ on a sulfonated polystyrene surface in the presence of 0.003 µg/ml ferric ions.
Figure 11B:
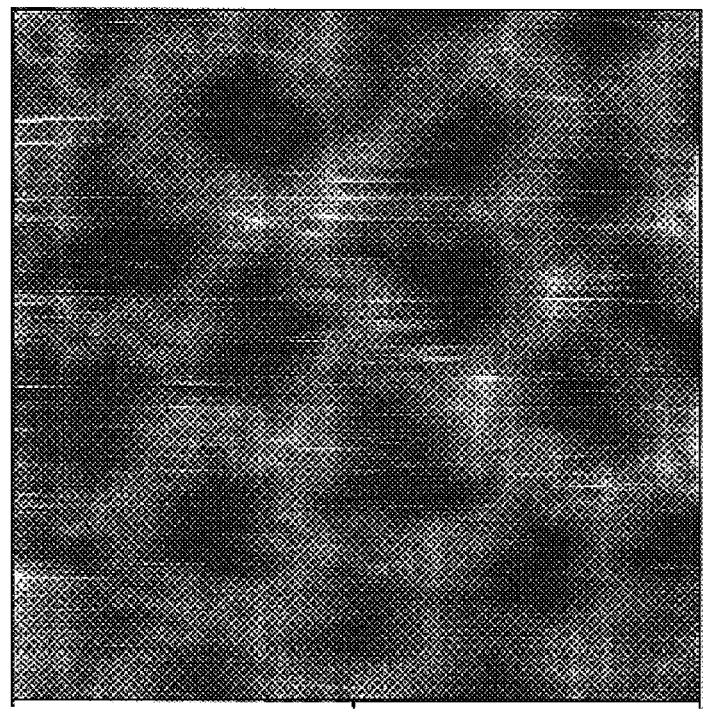
FIG. 11b depicts AFM imaged morphology of adsorbed fibronectin at 0.3 $C/m^2$ on a sulfonated polystyrene surface in the presence of 3 µg/ml ferric ions.
Figure 12:
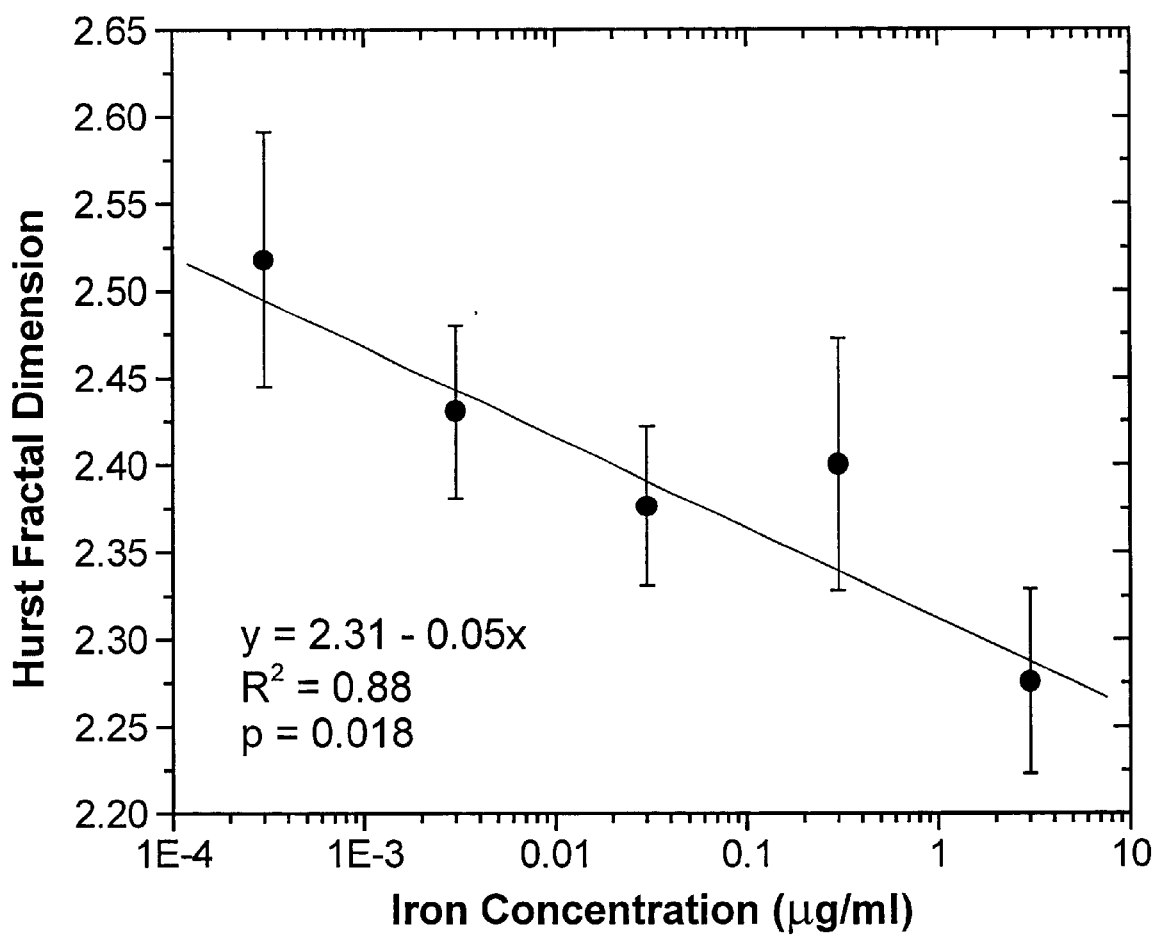
FIG. 12 is a graphic depiction of fractal dimensions of matrices formed under a range of iron exposures (Fe+3). $R^2$ is the correlation coefficient. P is the probability that the line is horizontal. y is the y-axis.

The effect of ferric (Fe+3) ions on fibronectin matrix formation was studied in accordance with the present invention. To accomplish this, fibronectin is combined with a buffered ferric ion aqueous solution and incubated with the charged material. After incubation for a suitable period of time, the morphology of the resulting construct is examined. As can be seen from FIGS. 11*a* and 11*b*, ferric ions have a clearly discernable influence on the morphology of fibronectin matrix as compared to a uncontaminated fibronectin matrix. See, e.g., FIG. 2*d*. FIG. 11*a* shows a fibronectin matrix formed in the presence of 0.003 µg/ml iron and FIG. 11b shows a fibronectin matrix formed in the presence of 3 µg/ml iron. The images are 100 microns across. The results can be quantified using fractal analysis using, e.g., the procedures disclosed in Russ, (1993) *Fractal Surfaces*, Plenum Press, N.Y. FIG. 12 depicts the fractal dimensions of matrices formed under a range of iron exposures.

The following Examples are included merely for purposes of illustrating certain aspects of the invention and should not be taken as limiting the invention in any manner whatsoever.

EXAMPLE 1

Polished 200 micron silicon wafers (Wafer World Corporation, West Palm Beach, Fla.) were partitioned into 1×1 cm samples. The wafers were cleaned and treated to be hydrophilic using the modified Shiraki technique. To accomplish this, the substrate was immersed in $H_2O:H_2O_2:NH_4OH$ (4:1:1, v:v:v) for 5 minutes at 80° C., then rinsed in deionized water and immersed in $H_2O:HF$ (3:1, v:v) for 30 seconds at room temperature to produce a hydrophobic surface. The wafers were then rinsed again in deionized water and immersed into $H_2O:H_2O_2:H_2SO_4$ for 10 minutes at 80° C. to produce a hydrophilic surface. NaCl neutralized sulfonated polystyrene random copolymers were synthesized with sulfonation levels ranging from 0% to about 30%. Sulfonated polystyrene (SPS) was dissolved in dimethylformamide (DMF) (8–10 mg/ml) and polystyrene (PS) in toluene and these solutions were spun cast (2500 rpm) onto the silicon wafers producing sulfonated polystyrene layers of about 500–1000 angstroms (Headway, Inc., photoresist spinner) with thickness controlled by varying polymer concentration. The PS and SPS coated wafers were vacuum annealed at 180° C. and 150° C., respectively for 24 hours. The wafers were then washed with deionized water and air dried under sterile conditions prior to use. Final film thickness was measured using ellipsometry (Rudolph, Inc., Auto EL). The film thickness preferred for shielding the influence of the silicon substrate is approximately 500 angstroms. AFM topology images of these films showed surface roughness to be 12 angstroms or less.

Sulfonation ranged from 0–30% as determined by mass spectroscopy (Desert Analytics, Tucson, Ariz.) with conversion to percent sulfonation utilizing a molecular weight for sulfur of 32 g/mol, 183 g/mol for sulfonate styrene group and 104 g/mol for styrene. Average surface charge density was calculated assuming a uniform distribution of charges along the chain. A Gaussian approximation was used to estimate the radius of gyration of the chain, from which the area that each chain occupies on the surface was extracted, yielding a 0.0065 Coulomb/$m^2$ charge density for each percentage of sulfonation. Tissue culture plastic (TCPS) and petri dish (PD) surface charge density was measured utilizing a vibrating electrode in air. Unsulfonated polystyrene was assumed to support a charge density of less and $10^{-7} C/m^2$, which represents the resolution of measurement sensitivity.

EXAMPLE 2

Bovine fibronectin (Sigma) at 100 µg/ml of phosphate-buffered (pH=7.2) saline solution (100 µg/ml) with 1% penicillin was incubated with the surfaces from Example 1 at 37° C., 100% humidity, 5% $CO_2$ for up to 72 hours. Protein concentration was measured by absorption spectroscopy at 562 nm after reaction with BCA protein assay (Pierce). Surface charge density in aqueous media was controlled by varying the degree of sulfonation from 0% to 23%, providing surface charge densities ranging from 0 to −0.15 $C/m^2$. Adsorption onto bacteriologic grade polystyrene (PD) and tissue culture grade polystyrene dishes (TCPS), which support net surface charge densities below $10^{-5}$ $C/m^2$ was also evaluated.

Surfaces with adsorbed protein layers were imaged by AFM (Thermomicroscopes TMX 2000 Explorer STM) under phosphate buffer solution by contact mode. AFM imaging also permitted a thickness measurement of the adsorbed protein layer. The thickness of the fibronection base-layer was accomplished by ablating the adsorbed layer with an AFM tip by applying a high force and then rescanning the region under normal contact mode. Adsorbed layer thickness was determined by comparison of elevations in the ablated region to the local unperturbed region. See FIG. 3. Note that ablation results in ridge formations at the edges of the ablated region.

Monolayer adsorption (22 ng/$mm^2$) was observed for charge densities up to 0.03 $C/m^2$, and an abrupt transition to multiplayer adsorption at higher charge densities. In FIG. 1, the magnitude of the charge density is represented on the abscissa, sulfonated surfaces have a net negative charge density. FIGS. 2a–2d demonstrate that the morphology adsorbed fibronectin, as imaged by AFM was dependent on surface charge density. In FIGS. 2a–2d, surfaces were imaged by contact made under PBS and each image is 20×20 µm.

EXAMPLE 3

Spin coated wafers prepared in accordance with Example 1 were utilized to assess the influence of ferric (Fe+3) ions on fibronectin matrix formation. Ferric sulfate powder was dissolved into water to form a 1 mg/ml solution which was diluted into PBS solutions to achieve concentrations of from $10^-$ to 10 µg/ml.

Bovine fibronectin (sigma) was added to the PBS iron solutions to a concentration of 100 µg/ml (pH 7.2, 1% penicillin). Spin coated wafers were placed into 35 mm dishes and submerged in 2.4 ml of the fibronectin/ferric ion solution at 37° C., 100% humidity, in a $CO_2$ free light free environment for 96 hours. Results are shown in FIGS. 11a, 11b and 12. The ferric ion is shown to have a pronounced effect on fibronectin matrix formation.

It will be understood that various modifications may be made to the embodiments and/or examples disclosed herein. Thus, the above description should not be construed as limiting, but merely as exemplifications of preferred embodiments. Those skilled in the art will envision other modifications within the scope and spirit of the claims appended hereto.

What is claimed is:

1. A method for causing aggregation of a polyampholyte selected from the group consisting of fibronectin molecules, aggrecan molecules, vitronectin molecules, tenascin molecules, elastin molecules and laminin molecules, comprising subjecting the polyampholyte molecules to a charge density of greater than about 0.01 $C/m^2$ generated by a non-living system to cause aggregation of the polyampholyte molecules.

2. A method according to claim 1 wherein the aggregation is characterized by formation of a globular form of fibronectin.

3. A method according to claim 1 wherein the aggregation is characterized by formation of fibrils of fibronectin.

4. A method according to claim 3 wherein the fibrils of fibronectin form a network.

5. A method according to claim 1 wherein aggregation is characterized by formation of fibrils of aggrecan.

6. A method according to claim 5 wherein the fibrils of aggrecan form a network.

7. A method according to claim 1 wherein the charge density is greater than about 0.1 $C/m^2$.

8. A method according to claim 1 wherein the charge density is greater than about 0.15 $C/m^2$.

9. A method according to claim 1 wherein the charge density is initially generated at a charged surface.

10. A method according to claim 9 wherein the charge is generated by a charged polymer.

11. A method according to claim 10 wherein the charge polymer is sulfonated polystyrene.

12. A method according to claim 10 wherein the charge polymer is adhered to a substratum.

13. A method according to claim 12 wherein the substratum is a flat surface.

14. A method according to claim 12 wherein the substratum is a silicon wafer.

15. A method according to claim 1 wherein the step of subjecting the polyampholyte to a charged density occurs in an aqueous environment.

16. A method according to claim 15 further comprising adjusting the charge density to cause fibrillogenisis based on the amount of salt contained in the aqueous environment.

17. A composition comprising a synthetic surface having a charge density greater than about 0.01 $C/m^2$ in contact with a polyampholyte selected from the group consisting of fibronectin, aggrecan, vitronectin, tenascin, elastin and laminin.

18. A composition according to claim 17 wherein the charge density greater than about 0.1 $C/m^2$.

19. A composition according to claim 17 wherein the charge density is greater than about 0.15 $C/m^2$.

20. A composition according to claim 17 wherein the charge is generated by a charged polymer.

21. A composition according to claim 20 wherein the charged polymer is sulfonated polystyrene.

22. A composition according to claim 17 wherein the synthetic surface comprises a layer of charged polymer adhered to a substratum.

23. A composition according to claim 22 wherein the substratum is silicon.

24. A composition according to claim 17 further comprising an aqueous solution containing salt.

25. A composition according to claim 24 wherein the salt is selected from the group consisting of monovalent salt, divalent salt, trivalent salt and combinations thereof.

26. An aggregated polyampholyte possessing substantially fibrillar morphology wherein the polyampholyte is selected from the group consisting of fibronectin molecules, aggrecan molecules, vitronectin molecules, tenascin molecules, elastin molecules and laminin molecules.

27. An aggregated polyampholyte produced in accordance with the method of claim 1 wherein the aggregated polyampholyte possesses substantially fibrillar morphology.

28. The aggregated polyampholyte of claim 27 wherein the polyampholyte is fibronectin.

29. The aggregated polyampholyte of claim 27 wherein the polyampholyte is aggrecan.

30. The aggregated polyampholyte of claim 27 wherein the polyampholyte is vitronectin.

31. The aggregated polyampholyte of claim 27 wherein the polyampholyte is tenascin.

32. The aggregated polyampholyte of claim 27 wherein the polyampholyte is elastin.

33. The aggregated polyampholyte of claim 27 wherein the polyampholyte is laminin.

* * * * *